United States Patent [19]

Throckmorton

[11] 3,937,738

[45] Feb. 10, 1976

[54] (PERHALOALKYL) THIO-SUBSTITUTED ALDEHYDES AND KETONES

[75] Inventor: James R. Throckmorton, Woodbury, Minn.

[73] Assignee: Minnesota Mining and Manufacturing Company, St. Paul, Minn.

[22] Filed: Apr. 25, 1974

[21] Appl. No.: 464,492

[52] U.S. Cl...... 260/593 H; 260/601 H; 260/482 C; 260/586 R; 260/566 A; 71/106; 424/331
[51] Int. Cl.² ................... C07C 49/16; C07C 47/14
[58] Field of Search .................... 260/593 H, 601 H

[56] References Cited
FOREIGN PATENTS OR APPLICATIONS
2,240,223   6/1972   Germany ........................... 260/593

Primary Examiner—James O. Thomas, Jr.
Assistant Examiner—James H. Reamer
Attorney, Agent, or Firm—Alexander, Sell, Steldt & DeLaHunt

[57] ABSTRACT

Perhaloalkanesulfenyl chlorides are reacted with aldehydes and ketones to provide novel (perhaloalkyl)thio-substituted aldehydes and ketones which are useful organic solvents and intermediates. As intermediates, these compounds are especially useful in the preparation of their carbamate derivatives which have pestical utility.

5 Claims, No Drawings

(PERHALOALKYL) THIO-SUBSTITUTED ALDEHYDES AND KETONES

BACKGROUND OF THE INVENTION

1. Field of the Invention

This invention relates to novel (perhaloalkyl)thio-substituted aldehydes and ketones which are prepared by reacting the unsubstituted aldehyde or ketone with a perhaloalkanesulfenyl chloride. A further aspect of the invention relates to a novel process for preparing (perhaloalkyl)thio-substituted carbamates utilizing the aldehydes and ketones of the invention as essential intermediates. These carbamate derivatives have useful pesticidal activity.

2. Prior Art

Carbamate derivatives of ketoximes have been disclosed by Magee (U.S. patent application, Ser. Nos. 132,584 now abandoned and 229,207 now U.S. Pat. No. 3,875,232). Some of the carbamate compounds described therein contain alkylthio-substituents. The corresponding alkylthiosubstituted ketones from which these compounds are derived are prepared by a different method from that of the present invention. Instead of reacting the unsubstituted ketone with a sulfenyl chloride, the ketones are prepared by reacting a haloketone with a mercaptan in the presence of an acid receptor. No halogen-containing alkylthio-substituted ketones are disclosed by this reference, and although the compound 1-(3,3,3-trifluoropropylthio)-3,3-dimethyl-2-butanone O-methylcarbamoyloxime is mentioned, no method is given for its preparation, and the ketone starting material from which this compound is prepared is not disclosed.

Payne and Weiden [J. Ag. and Food Chem., 14 356 (1966)] have reported the preparation of trisubstituted acetaldehyde O-(methylcarbamoyl)oximes wherein one of the substituents may be an alkylthio group. The process utilized to obtain the aldehyde precursors of these compounds does not include a sulfenyl chloride as one of the reactants, and no halogen-containing alkylthio-substituted aldehydes are disclosed by this reference.

The reactivity of perhaloalkanesulfenyl chlorides is summarized by Karasch, The Chemistry of Organic Sulfur Compounds, Vol. 2, 137–165 (1966). No reactions of perhaloalkanesulfenyl chlorides with either aldehydes or ketones are given in this discussion. The reaction of trifluoromethanesulfenyl chloride with the ester compound sodium formyl acetic acid ester has been reported by Haas et al., Chem. Ber., 104, 1855 (1971).

Leir, J. Org. Chem., 37, 887 (1972) reported the reaction of disulfenyl chlorides with aldehydes and active methylene compounds. In this reference the difficulty of producing the substituted aldehyde without the occurrence of polymerization is discussed.

The reaction of sulfenyl chlorides, in general, with compounds containing active methylene groups is summarized by E. Kuhle, Synthesis, 1971, 617. Reaction of ethanesulfenyl chloride with acetone was found to yield hexaalkylthio-substituted acetone, Brintzinger et al., Chem. Ber. 87, 300 (1954). Chloroethanesulfenyl chloride is shown to react with acetone to produce chloroethylthioacetone, Fuson et al., J. Org. Chem. 11, 469, (1946).

From the above discussion of the prior art, one may be led to conclude that perhaloalkanesulfenyl chlorides would react with aldehydes and ketones in the same manner as nonperhalogenated alkanesulfenyl chlorides. However, this has not been found to be the case. For example, when methanesulfenyl chloride was reacted with tert-butyl methyl ketone, according to art-recognized procedures, (i.e. those prescribed for the reaction of ethanesulfenyl chloride with acetone), no reaction product could be obtained. It was therefore surprising to find that by substituting a perhaloalkanesulfenyl chloride for the nonperhalogenated reactant, the reaction proceeded without difficulty, and a perhaloalkylthio-substituted ketone was in fact obtained.

When nonperhalogenated alkanesulfenyl chlorides are reacted with aldehydes and ketones, e.g. acetone, the molar ratio of reactants is critical. Excess amounts of the sulfenyl chloride tend to produce poly-substituted alkythio-aldehydes and ketones, e.g. hexalkylthio-substituted acetone. When perhaloalkanesulfenyl chlorides are reacted with aldehydes and ketones according to the present invention, an excess amount of the sulfenyl chloride is not detrimental to the formation of monosubstituted products. The process of preparing compounds of the present invention minimizes the uncontrolled formation of poly-substituted alkylthio-substituted aldehydes and ketones.

The compounds of the present invention exhibit superior stability characteristics over known alkylthio-substituted aldehydes and ketones. This superiority is especially evident with respect to stability against oxidation.

A recent publication by Bayreuther and Haas, Chem. Ber., 106, 1418 (1973) describes the preparation of certain trifluoromethylthio-ketones through the use of trifluoromethanesulfenyl chloride. However, prior to the present invention, it is believed that perhaloalkylthio-substituted aldehydes or ketones have not been described.

SUMMARY OF THE INVENTION

The aldehyde and ketone compounds of the present invention can be expressed by the formula:

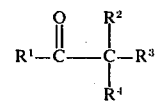

wherein $R^1$ is H, $-CH_3$, or $-CH_2SCF_3$; $R^2$ and $R^3$ are H, $-CH_3$ or together with the carbon atom to which they are attached form a six-membered cycloaliphatic ring; and $R^4$ is $CF_3S-$ or $CFCl_2S-$.

The perhaloalkylthio-substituted ketones and aldehydes of the invention are readily prepared by reacting the corresponding unsubstituted aldehyde or ketone with a perhaloalkanesulfenyl halide in an inert solvent. The mole ratio of ketone or aldehyde to sulfenyl chloride can range from about 2:1 to about 1:2, but preferably equimolor amounts of starting materials are used. Excess perhaloalkanesulfenyl chloride is not detrimental since significant polysubstitution does not readily occur.

The presently preferred solvents for use in the reaction are chlorinated hydrocarbons such as chloroform, dichloromethane and the like. Other suitable solvents are acetonitrile, ethyl acetate, methyl acetate, benzene and nitromethane. It is presently preferred to add to the reaction mixture as a catalyst small amounts, i.e. less than ten mole percent with respect to the reactants, of an alcohol such as methanol, ethanol, isopropanol, or n-hexanol. The effect of the catalyst is to increase the rate and yield of the reaction.

The temperature of the reaction mixture may range from about −78°C to the reflux temperature of the reaction mixture, i.e. up to about 125°C. The preferred temperature range is from −25 to +50°C.

The reaction may be run under pressure to provide safer and more efficient confinement of the reactants.

Purification and isolation of the liquid products is generally carried out by distillation, column chromatography and/or vapor phase chromatography.

The (perhaloalkyl)thio-substituted ketones of the invention are useful solvents, particularly for halogenated, e.g. fluorinated or chlorinated, organic compounds. The compounds of the invention show good stability, especially to oxidation. The ketones and aldehydes may also be intermediates, e.g. they may be reduced to alcohols or oxidized to acids. Some of the ketone compounds of the invention may be reduced to alcohols which can be converted to phenyl carbamates having herbicidal activity. As intermediates the compounds of the invention are especially useful in the preparation of carbamates which are pesticides. The most preferred compounds for use as intermediates in preparing pesticidal carbamates are:

2-methyl-2-trifluoromethylthiopropionaldehyde
1-trifluoromethylthio-3-methyl-2-butanone In order to prepare their carbamate derivatives, the aldehydes and ketones of the invention must first be converted to oximes by replacing the oxygen atom of the aldehyde or ketone with a NOH substituent. This conversion is accomplished by reaction of the compounds with hydroxylamine, generally as the hydrochloride. Approximately equimolor amounts of starting materials are used.

This oximination reaction requires a suitable solvent such as an aqueous alcohol e.g., ethanol, a halogenated hydrocarbon, e.g. dichloromethane and the like. The reaction is preferably carried out in the presence of an acid acceptor such as an organic base, e.g. a tertiary amine such as triethylamine, or an inorganic base, e.g. sodium carbonate.

Isolation and purification of the oxime products are generally accomplished by the use of standard synthetic techniques such as extraction, column chromatography, recrystallization or distillation.

To produce the final carbamate product, the NOH group of the oxime must be converted to

Two convenient methods are available to effect this conversion.

The most preferred of these alternative methods, herein termed Process A, consists of reacting the oxime with methyl isocyanate. This reaction is carried out in an inert organic solvent and preferably in the presence of a tertiary amine catalyst. The inert organic solvents that can be employed in the reaction are those which are generally inert to isocyanates, i.e. free of substituents such as amino or hydroxy groups. Examples of useful solvents are aliphatic ketones such as acetone; aliphatic and aromatic hydrocarbons such as hexane, benzene, heptane, octane, toluene and the like; ethers such as diethyl ether and ethyl n-propyl ether; and chlorinated hydrocarbons such as dichloromethane. Suitable catalysts are aliphatic and/or aromatic tertiary amines such as dimethylaniline, triethylamine or the like. Generally, amounts of tertiary amine catalyst ranging from about 0.1 to about 1.0 weight percent of the starting materials comprised of the oxime and methyl isocyanate are sufficient.

The reaction may be effected at temperatures ranging from 10°C to about 130°C and is preferably carried out between 25°C and 80°C. The pressure used is generally one atmosphere, although the reaction can be carried out at higher pressures if desired.

The molar ratio of isocyanate to oxime can range from about 0.25:1 to about 2:1, but preferably an equimolar amount or slight excess of the isocyanate is employed to ensure that the oxime is completely reacted. The reaction time for substantial completion may vary from about 5 minutes to about 7 days, depending upon the reaction temperature and the amount of oxime used. Normally when operating in the preferred temperature range, reaction times of from about one-half hour to about 3 days are sufficient for complete reaction.

According to the second alternative method for converting the oximes to carbamates, herein termed Process B, the oxime is reacted with phosgene in an inert solvent such as toluene or diethyl ether, in the presence of an acid acceptor such as a suitable amine, e.g. dimethylaniline. The molar ratio of oxime to phosgene is approximately 1:1, and the amount of acid acceptor is approximately equimolar to the phosgene used.

This reaction can be carried out at from −30°C to about 40°C, but will generally be found to proceed most advantageously between −10°C and about 25°C. The reaction is slightly exothermic so that some external cooling is usually necessary to maintain the temperature within the desired range. The reaction mixture can be filtered or washed with water to remove the byproduct amine hydrochloride, and the organic layer containing the chloroformate is then further reacted with methylamine. The reaction of the chloroformate intermediate with methylamine is carried out in the presence of solvents for the intermediate such as diethyl ether, dioxane, toluene or chloroform, at temperatures between about −40°C and about 80°C. Preferably the temperature is maintained below 40°C because the reaction proceeds smoothly, even at low temperatures, and is so rapid above 40°C that loss of low boiling reactants may occur and some decomposition may take place.

The carbamate products formed in Process A or Process B are solids which can be recovered from the reaction mixture by means known to the art, such as extraction or vacuum distillation to remove the solvent.

The carbamate derivatives of the aldehydes and ketones of the present invention are useful pesticides and show activity as insecticides, acaricides, and/or nematicides. This physiological activity has been established by standard screening methods.

The invention will be further understood by reference to the following illustrative and nonlimiting examples. All melting points and boiling points given are uncorrected.

EXAMPLE 1

Preparation of
2-Dichlorofluoromethylthio-2-methylpropionaldehyde

A mixture of isobutyraldehyde (0.22 mole), dichlorofluoromethanesulfenyl chloride (0.2 mole) and chloroform (100 ml) was refluxed for twenty-four hours. Distillation of the reaction mixture gave 2-dichlorofluoromethylthio-2-methylpropionaldehyde, b.p. 60°–67°C/7 mm. The structure was confirmed by spectral and elemental analyses of a purified sample, b.p. 72°C/10 mm Hg.

EXAMPLE 2

Preparation of
2-Trifluoromethylthio-2-methylpropionaldehyde

A mixture of isobutyraldehyde (0.25 mole), ethanol (0.4 g) and dichloromethane (75 ml) was placed in a three-necked flask fitted with a gas inlet tube, a Dry Ice condenser and a gas outlet tube connected to a gas trap cooled to −78°C. Trifluoromethanesulfenyl chloride (0.22 mole) was added to the cold solution which was maintained under a nitrogen atmosphere. (Caution: It should be noted that trifluoromethanesulfenyl chloride is a highly hazardous material which must be handled with care to avoid inhalation or contact with the skin.) The reaction mixture was then allowed to warm to about 25°C and stirred magnetically until the orange colored solution had become nearly colorless (about 6 hours). The reaction mixture was then distilled. The distillation assembly was connected to a −78°C gas trap to trap any unreacted trifluoromethylsulfenyl chloride. The 2-trifluoromethylthio-2-methylpropionaldehyde, b.p. 108°–116°C was identified by spectral and elemental analyses of a purified sample, b.p. 116°C.

EXAMPLE 3

Preparation of
2-Trifluoromethylthio-2-methylpropionaldehyde

A mixture of isobutyraldehyde (0.75 mole), ethanol (1.2 g) and dichloromethane (200 ml) was introduced into a sealed and pressure tested two-liter vessel under reduced pressure. Trifluoromethanesulfenyl chloride (0.7 mole) was then added to the cooled, evacuated vessel. The vessel was warmed to about 25°C and then rocked for two and a half to three days. The vessel was vented through a cold gas trap (−78°C) to trap any unreacted trifluoromethylsulfenyl chloride, and through a scrubbing system to remove the vented hydrogen chloride gas. Residual liquid was transferred to a flask and distilled to give 67 g. of the desired product, 2-trifluoromethylthio-2-methylpropionaldehyde. The structure of the product was confirmed by spectral and elemental analyses.

EXAMPLE 4

Preparation of
1-Trifluoromethylthio-3-methyl-2-butanone and
3-Trifluoromethylthio-3-methyl-2-butanone Using the method described in Example 3, 3-methyl-2-butanone was reacted with trifluoromethanesulfenyl chloride to provide a reaction product which was distilled. The product had a boiling point of 51° to 84°C/48 mm. Vapor phase chromatography of this distillate showed two products to be present in major quantities. Fractional distillation of this product provided 3-trifluoromethylthio-3-methyl-2-butanone, b.p. 68°C/54 mm Hg and 1-trifluoromethylthio-3-methyl-2-butanone, b.p. 84°C/54 mm Hg. The structures of these compounds were determined by spectral and elemental analyses.

EXAMPLE 5

Preparation of 3-Trifluoromethylthio-2-butanone and
1-Trifluoromethylthio-2-butanone Using the method of Example 3, 2-butanone was reacted with trifluoromethanesulfenyl chloride. The reaction mixture was distilled, b.p. 30°–72°C/55 to 60 mm. Vapor phase chromatography of the distillate showed two products to be present in major quantities. Fractional distillation gave 3-trifluoromethylthio-2-butanone, b.p. 66°C/62 mm Hg, and 1-trifluoromethylthio-2-butanone, b.p. 85°C/62 mm Hg. These structures were established by spectral and elemental analyses.

EXAMPLE 6

Preparation of
1,1-bis(trifluoromethylthio)-2-propanone and
1,3-bis(trifluoromethylthio)-2-propanone Using the method of Example 3, a mixture of 1-trifluoromethylthio-2-propanone (0.15 mole), dichloromethane (75 ml), ethanol (0.3 g) and trifluoromethanesulfenyl chloride was loaded into a sealed metal reaction vessel. The reaction was carried out for 67 hours at room temperature. Most of the dichloromethane was removed by distillation. Vapor phase chromatography of the residual liquid showed about 55 percent unreacted 1-trifluoromethylthio-2-propanone and two products. The distillation residue was returned to the sealed metal reactor, 11.2 g (0.082 mole) of trifluoromethanesulfenyl chloride and 75 ml of dichloromethane were added, and the reaction was allowed to continue for 12 days at room temperature. The dichloromethane was removed by distillation and the residue was examined by vapor phase chromatography. This analysis showed only 16% unreacted starting material. Fractional distillation of the reaction mixture gave 1,1-bis(trifluoromethylthio)-2-propanone, b.p. 44°C/23 mm Hg and 1,3-bis(trifluoromethylthio)-2-propanone, b.p. 67°C/5 mm Hg. These structures were established by elemental and spectral analyses.

EXAMPLE 7

Preparation of the carbamate derivative of the ketone
1-Trifluoromethylthio-2-propanone Step 1

A mixture of 2-propanone (0.25 mole), ethanol (0.49) and dichloromethane (75 ml) was introduced into a sealed and pressure tested vessel having a volume of about 500 ml under reduced pressure. Trifluoromethanesulfenyl chloride (0.22 mole) was then added to the cooled, evacuated vessel. The vessel was warmed to about 25°C and then rocked for five days. The vessel was vented through a cold gas trap (−78°C) to trap any unreacted trifluoromethylsulfenyl chloride gas and then through a scrubbing system to remove the vented hydrogen chloride gas. Residual liquid was transferred to a flask and distilled to give about 24 g of 1-trifluoromethylthio-2-propanone. The structure of the purified product (b.p. 51°–52°C/22 mm Hg) was confirmed by spectral and elemental analyses.

Step 2

A mixture of hydroxylamine hydrochloride (0.12 mole) in ethanol (125 ml), sodium carbonate (0.06 mole) in 65 ml of water and 1-trifluoromethylthio-2-propanone (0.11 mole) from Step 1 was stirred at room temperature overnight. The reaction mixture was poured into water, the oxime was extracted into diethyl ether, the combined ether extracts were washed with water and then dried. The drying agent was removed by filtration and the filtrate was distilled to provide 2-trifluoromethylthio-2-propanone oxime, b.p. 57°–58°C/1.6 mm Hg. The structure of this product was confirmed by elemental and spectroscopic analyses.

Step 3 (Process A)

A mixture of 1-trifluoromethylthio-2-propanone oxime (0.02 mole) from Step 2, methyl isocyanate (0.22 mole) and 2 drops of triethylamine in 25 ml of dichloromethane was heated at its reflux temperature overnight. The solvent was removed by evaporation under vacuum. The residual oil was recrystallized from a mixture of petroleum ether and diethyl ether to give a pure sample of 1-trifluoromethylthio-2-propanone O-methylcarbamoyl oxime, m.p. 56°–58°C. The structure of the product was confirmed by elemental and spectral analyses.

Step 3 (Process B)

To a cold (0°–5°C) benzene solution of phosgene (23.2 g of 12.5% solution, i.e. 0.03 mole phosgene) was added dimethylaniline (0.03 mole). To the cold mixture was added 1-trifluoromethylthio-2-propanone oxime (0.03 mole) from Step 2 and 60 ml of benzene. The reaction mixture was stirred for two hours at room temperature. Aqueous methylamine (0.03 mole) was then added to the reaction mixture. The reaction mixture was then washed with water and dried. Filtration to remove the drying agent was followed by evaporation of the solvents under vacuum to provide a residue which was purified by chromatography on silica gel and recrystallization. The structure was confirmed by spectral comparison of the product with the spectral characteristics of the product of Process A.

EXAMPLE 8

Preparation of the carbamate derivative of 2-trifluoromethylthio-2-methylpropionaldehyde Step 1

Preparation of the aldehyde according to Example 2.

Step 2

A mixture of hydroxylamine hydrochloride (0.09 mole) in methanol (230 ml), sodium carbonate (4.8 g, 0.045 mole) in 50 ml of water and 2-trifluoromethylthio-2-methylpropionaldehyde (14.85 g, 0.086 mole) from Step 1 was stirred at room temperature overnight. The reaction mixture was poured into water, the oxime was extracted into diethyl ether, the combined ether extracts were washed with water and then dried. The drying agent was removed by filtration and the filtrate was distilled to provide 2-trifluoromethylthio-2-methylpropionaldehyde oxime, b.p. 80°C/18 mm. The structure of this product was confirmed by elemental and spectroscopic analyses.

Step 3

2-Trifluoromethylthio-2-methylpropionaldehyde oxime from Step 2 was reacted with methyl isocyanate according to the method of Example 7, Step 3, Process A. The carbamate product was found to have a melting point of 29°–30°C and its structure was confirmed by elemental and spectroscopic analyses.

The following examples illustrate additional compounds of the invention prepared according to the synthetic methods illustrated in Example 3.

Example 9

| Structure | Boiling Point (°C/mmHg) | Elemental Analysis (Calculated/Found) |
|---|---|---|
| CF$_3$SCH$_2$—CH=O (CH$_3$) | 61°/150 | C, 30.38; H, 3.19<br>C, 30.4 ; H, 3.3 |

Example 10

| Structure | Boiling Point (°C/mmHg) | Elemental Analysis (Calculated/Found) |
|---|---|---|
| CF$_3$S—⌬—CHO | 35°/0.35 | C, 45.27; H, 5.22<br>C, 45.5 ; H, 5.2 |

What is claimed is:

1. A compound of the formula:

$$R'-\overset{O}{\overset{\|}{C}}-\underset{R^4}{\overset{R^2}{\underset{|}{C}}}-R^3$$

wherein R' is —CH$_3$ or —CH$_2$SCF$_3$; R$^2$ and R$^3$ are H or —CH$_3$; and R$^4$ is —CH$_3$, CF$_3$S or CFCl$_2$S—, except that when R' is —CH$_3$, R$^4$ is not —CH$_3$.

2. A compound according to claim 1 wherein R' is —CH$_3$.

3. The compound 1-trifluoromethylthio-3-methyl-2-butanone according to claim 2.

4. A process for the preparation of perhaloalkylthio-substituted ketones and aldehydes of the formula:

$$R'-\overset{O}{\overset{\|}{C}}-\underset{R^4}{\overset{R^2}{\underset{|}{C}}}-R^3$$

wherein R' if H, —CH$_3$ or —CH$_2$SCF$_c$; R$^2$ and R$^3$ are H, —CH$_3$ or together with the carbon atoms to which they are attached form a six-membered cycloaliphatic ring; and R$^4$ is —CH$_3$, CF$_3$S or CFCl$_2$S—, except that when R' is CH$_2$SCF$_3$, R$^4$ must be —CH$_3$, and when R' is —CH$_3$, R$^4$ is not CH$_3$, comprising reacting an aldehyde or ketone of the formula $$R'-\overset{O}{\overset{\|}{C}}-\underset{H}{\overset{R^2}{\underset{|}{C}}}-R^3$$

with a perhaloalkanesulfenyl chloride selected from the group consisting of CF$_3$SCl and CFCl$_2$SCl in a solvent inert to the reactants, at a temperature of −78° to 125°C and in an inert atmosphere.

5. A process according to claim 4 wherein an alkanol catalyst is added to the reaction mixture.

\* \* \* \* \*